United States Patent [19]

Biber et al.

[11] Patent Number: 4,715,704

[45] Date of Patent: Dec. 29, 1987

[54] LIGHT TRAP FOR SURGICAL OPERATION MICROSCOPES

[75] Inventors: Klaus Biber, Aalen; Gerhard Unold, Essingen, both of Fed. Rep. of Germany

[73] Assignee: Carl-Zeiss-Stiftung, Heidenheim, Fed. Rep. of Germany

[21] Appl. No.: 921,596

[22] Filed: Oct. 21, 1986

Related U.S. Application Data

[63] Continuation of Ser. No. 660,896, Oct. 15, 1984, abandoned.

[30] Foreign Application Priority Data

Oct. 28, 1983 [DE] Fed. Rep. of Germany ....... 3339172

[51] Int. Cl.$^4$ ............................ A61B 3/10; A61B 3/08
[52] U.S. Cl. ..................................... 351/207; 351/205
[58] Field of Search ..................... 351/205, 207, 206; 354/62

[56] References Cited

U.S. PATENT DOCUMENTS

| | | | |
|---|---|---|---|
| 3,259,041 | 7/1966 | Okajima | 351/207 |
| 4,247,176 | 1/1981 | Ito | 351/207 |
| 4,322,137 | 3/1982 | Nohda | 351/207 X |
| 4,439,024 | 3/1984 | Ito | 351/207 |

*Primary Examiner*—Rodney B. Bovernick
*Attorney, Agent, or Firm*—Stonebraker, Shepard & Stephens

[57] ABSTRACT

A microscope for examinations and surgical operations on the eye, having provision for projecting onto the eye a hollow beam of illuminating light, the beam having a dark center portion of the same diameter as the pupil of the eye. Thus the surgeon may have adequate illumination of the external surface of the eye around the pupil, without projecting light which might be disturbing or damaging to the patient, onto the retina or fundus of the eye. The light blocking structure, in the form of an annular diaphragm with a light-impervious central portion, is located in the illuminating light beam at a point which is conjugated with respect to the object plane, i.e., the plane of the pupil of the eye being examined. The diaphragm may be moved aside to an ineffective position when required.

1 Claim, 1 Drawing Figure

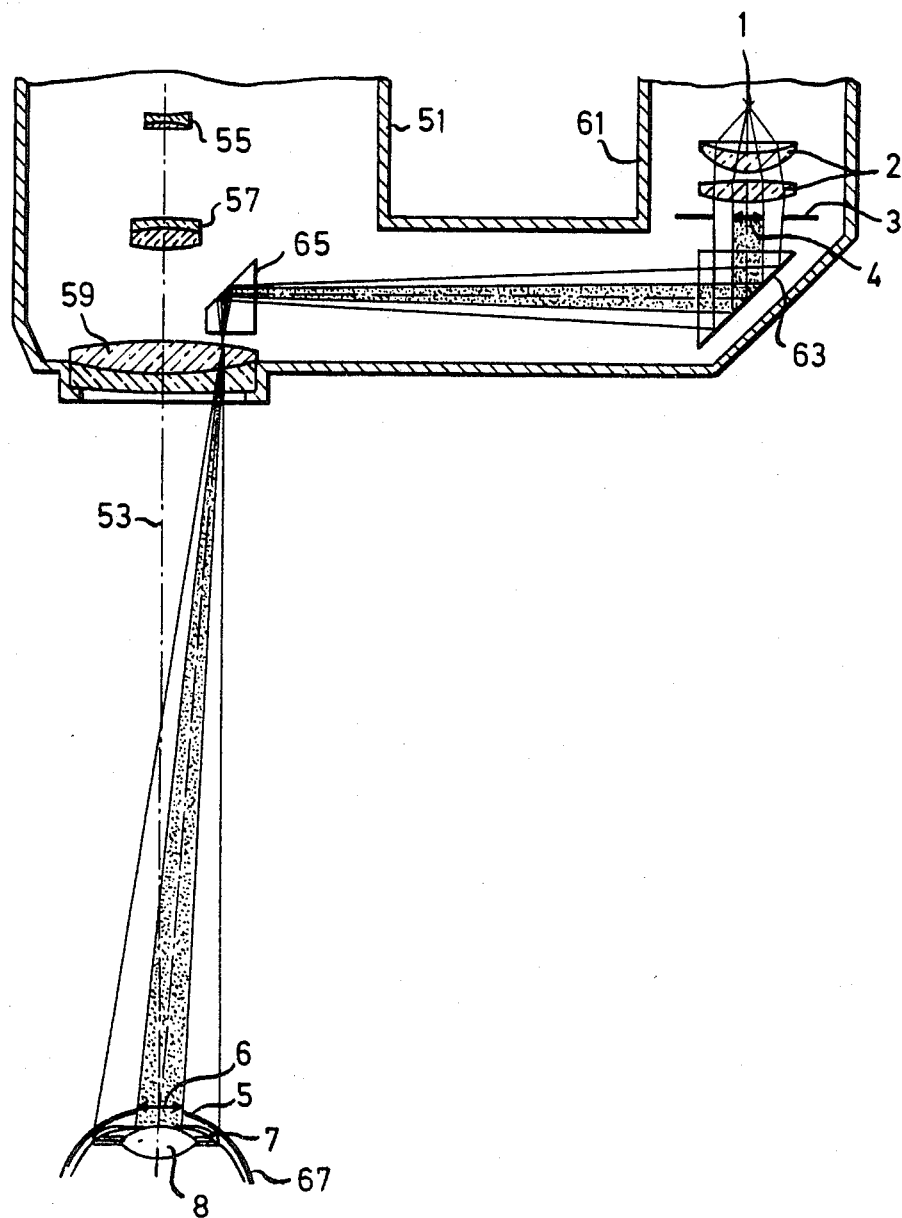

LIGHT TRAP FOR SURGICAL OPERATION MICROSCOPES

This application is a continuation of application Ser. No. 660,896, filed Oct. 15, 1984 now abandoned.

This invention relates to optical instruments used in examination or treatment of the eye, such for example as surgical microscopes, and relates more particularly to a light trap for preventing undesired rays from entering the eye when such instruments are being used. The surgeon or other user of the instrument obviously needs to have the eye illuminated sufficiently for the desired examination or operation. But when using an instrument with high intensity of light or other radiation, there is danger that the eye of the patient may be subjected to excessive illumination radiation. It is therefore necessary to take precautionary measures to prevent injury to or impairment of the eye of the patient.

It is already known to introduce a light trap in the form of a so-called "black spot" into the ray path of a fundus camera, to keep disturbing reflected light from the photosensitive material within the camera. See, for example, German Federal Republic Auslegeschrift (examined and published application) No. 1,951,159 (Okajima) of Dec. 13, 1973, and its counterpart U.S. Pat. No. 3,594,071 of July 20, 1971. Also see U.S. Pat. No. 4,102,563 (Matsumura) of July 25, 1978 (U.S. Class 351/7; International Class A61B 3/10) and its German Federal Republic counterpart Offenlegungsschrift (published application) No. 26 54 505 of June 8, 1977, which disclose an arrangement of two annular diaphragms, in an intermediate image plane of the illuminating system so that the images of these diaphragms are produced in the vicinity of the iris and on the lens of the eye. These prior art arrangements of the black spots and the annular diaphragms in the ray path are the result of what is desired in a fundus camera, namely, to protect the desired photographic image from undesired reflected light and undesired scattered light.

The object of the present invention, on the other hand, is to reduce the stress on the patient during an examination or an operation on his eye, by preventing the stream of light from the illuminating system from striking the retina of the eye.

This object is achieved by providing a light-blocking or light-absorbing layer arranged in a plane conjugate to the object plane, within the central region of the illumination ray path of a surgical microscope.

The light absorbing or blocking layer is preferably developed as a light-impervious central part of an annular diaphragm aperture. The diameter of this light-impervious central part is preferably so selected that the central vignetting produced on the eye of the patient corresponds to the diameter of the pupil of the patient's eye, which is usually widened or enlarged to a diameter of 8 mm for surgical operations.

The advantages resulting from this invention include particularly the fact that, on the one hand, with central vignetting of the patient's pupil the surgeon still has sufficient light for his examination or operation, while on the other hand the patient is not distressed by a stream of light impinging on his retina. Another advantage is that, with the illuminating device for a surgical microscope, the plane conjugate to the object plane is readily accessible from the outside, and the light absorbing or blocking layer can be applied, for instance, on a diaphragm which may optionally be swung or shifted into and out of the ray path from time to time. It is thus possible for the surgeon to use the illumination, if necessary, in its full intensity for a short period of time, and then, in the case of a lengthy operation, to relieve the patient by shifting the light blocking means into effective position, continuing the operation or treatment under reduced light conditions.

A preferred embodiment of the invention will be described in detail in connection with the annexed drawing.

BRIEF DESCRIPTION OF THE DRAWING

The single FIGURE is a fragmentary vertical section taken centrally through a portion of an operation microscope incorporating the present invention, showing also a patient's eye in the field of view of the microscope.

DESCRIPTION OF THE PREFERRED EMBODIMENT

In the drawing there is shown schematically the lower portion of the body or housing 51 of an operation microscope having an optical axis 53. Arranged on this optical axis are the usual optical elements, including lenses 55 and 57 and the objective 59. These parts may all be of the usual conventional construction, the details of which are unimportant for purposes of the present invention, and are subject to wide variation.

To provide illumination to enable the surgeon to see clearly the area being examined or operated upon, there is a source of light 1 mounted in a housing portion 61 which may be integral with, or separate from and attachable to and detachable from the main microscope housing 51, these details being immaterial for purposes of the present invention. Light from this source 1 passes through a condenser optical system 2 to form a broadened beam which is then reflected by the respective elements 63 and 65 (prisms or mirrors) to pass through a portion of the objective 59 and illuminate the object 67, which in this case is the eye of the patient. The eye is shown schematically as including the cornea 5, the iris 7, and the lens 8.

According to the invention, a field stop or diaphragm 3 is placed in the illuminating light beam at a location which is conjugate with respect to the object plane, this location being close to the condenser system 2 as illustrated. This field stop is preferably in the form of an annular diaphragm having a central light-absorbing or light-blocking layer, for instance a black spot 4. Thus the illumination light beam, after passing the stop, will be in the form of an annular beam of light, with a dark central core. The diameter of the light-obstructing central part 4 of the stop is so dimensioned that it produces on the cornea 5 of the patient a central vignetting or unlighted portion 6, the diameter of which corresponds to the diameter of the pupil of the patient's eye. Thus no light from the source 1 goes through the pupil to the fundus or retina of the eye, and the patient is not disturbed by the light, even though relatively bright light may be needed by the surgeon on the exterior surface of the eye surrounding the pupil.

The field stop 3 is mounted for movement into and out of its effective operating position, laterally by either a swinging movement on a pivot or a sliding movement on a track or in any other desired way, the details of which are not important and may be varied at will. Thus, as already stated above, the surgeon may temporarily move the stop aside if illumination of the eye's lens or the fundus from the source 1 is needed for brief intervals.

What is claimed is:

1. The method of illuminating an eye of a patient during surgery thereon, which comprises:
   (a) providing a surgical operation microscope having a microscope optical system which may be focused on an eye to be operated upon;
   (b) providing said microscope with an illumination system for projecting an illuminating beam of light onto said eye to be operated upon;
   (c) providing a shiftable blocking member shiftable between a blocking position and a non-blocking position with respect to said beam of light;
   (d) said blocking member when in its effective blocking position serving to intercept and block a central core portion of said beam of light to prevent the central core from reaching the eye to be operated upon while allowing a ring of light around said blocked central core to reach said eye, said blocked central core at the location where said beam impinges on the eye being substantially concentric with and of approximately the same size as the pupil of the eye, so that direct light of said beam will not enter the eye through the pupil and reach the retina and fundus portions of the eye;
   (e) said method further comprising keeping said blocking member in its said effective position during at least a substantial part of an operation on the eye, to relieve the patient of discomfort which would be caused by impingement of said illuminating beam onto the retina of the eye; and
   (f) moving said blocking member to its ineffective position only for brief intervals during the operation, only when additional illumination of the retina and fundus portions of the eye is temporarily needed.

* * * * *